United States Patent [19]

Ichikawa

[11] Patent Number: 4,981,482
[45] Date of Patent: Jan. 1, 1991

[54] DEVICE FOR FORMING AN INSERTING HOLE FOR AN ENDOSCOPE

[76] Inventor: Kazuo Ichikawa, 65-14, Okita, Wakabayashi Higashi-Cho, Toyota-Shi, Aichi-Ken, Japan

[21] Appl. No.: 349,769

[22] Filed: May 10, 1989

Related U.S. Application Data

[63] Continuation-in-part of Ser. No. 198,005, May 24, 1988, abandoned.

[30] Foreign Application Priority Data

Aug. 20, 1987 [JP] Japan ............... 62-126858

[51] Int. Cl.$^5$ ............................ A61M 29/00
[52] U.S. Cl. ...................... 606/108; 606/191; 604/104
[58] Field of Search ............ 606/45, 46, 108, 185, 606/197, 198, 191–194; 604/104

[56] References Cited

U.S. PATENT DOCUMENTS 4,705,041 11/1987 Kim ...................... 606/198 X
4,862,891 9/1989 Smith .................... 604/104 X

FOREIGN PATENT DOCUMENTS 10471 4/1971 Japan .
143439 9/1984 Japan .
174159 9/1985 Japan .

Primary Examiner—Robert A. Hafer
Assistant Examiner—Kevin G. Rooney
Attorney, Agent, or Firm—Fred Philpitt

[57] ABSTRACT

A tube device for forming a fistula is constructed in such a way that the tube device is composed of a metallic guide wire, a small diameter tube to which the guide wire can be inserted in its center, a medium diameter tube covering the outer periphery of the small diameter tube, a medium-large diameter tube covering the outer periphery of the small diameter tube and having an outer diameter larger than the medium diameter tube, a large diameter tube covering the outer periphery of the small diameter tube and having an outer diameter larger than the medium-large diameter tube, a large diameter drainage tube covering the outer periphery of the small diameter tube and having an outer diameter equal to that of the large diameter tube, and an extra large diameter tube covering the outer periphery of the large diameter drainage tube. An outer diameter of each tip portion of the small diameter tube, medium diameter tube, medium-large diameter tube and large diameter tube is gradually reduced towards ends thereof to be taper-shaped. These tubes are exchanged and inserted in the order of their diameters, i.e. from small diameter to large diameter, by means of a guide wire. The extra large diameter tube necessary for the insertion of the endscope can be inserted in a short time with an extreme safety since the tapered surface of the tip portion of the tube applies the pressure to the liver tissue to expand it gradually.

8 Claims, 3 Drawing Sheets

U.S. Patent  Jan. 1, 1991  Sheet 1 of 3  4,981,482
FIG. 1
FIG. 2
FIG. 3
FIG. 4
FIG. 5
FIG. 6
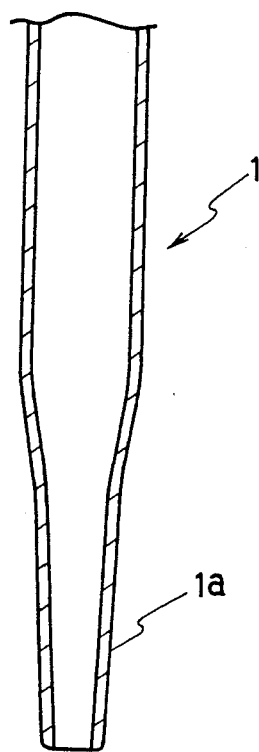
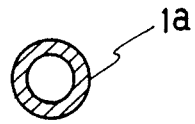
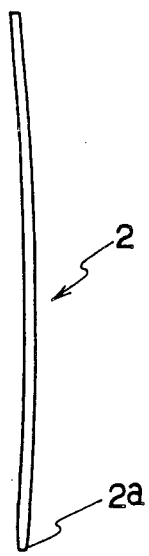
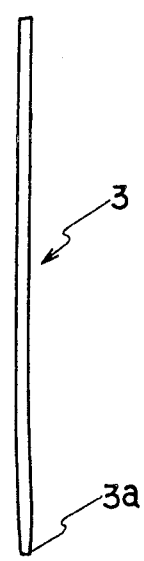
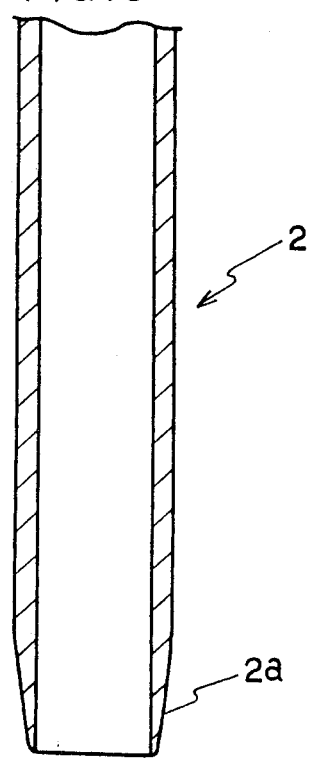

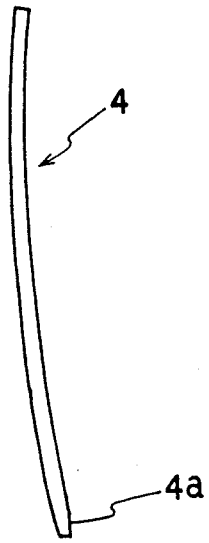
FIG.7
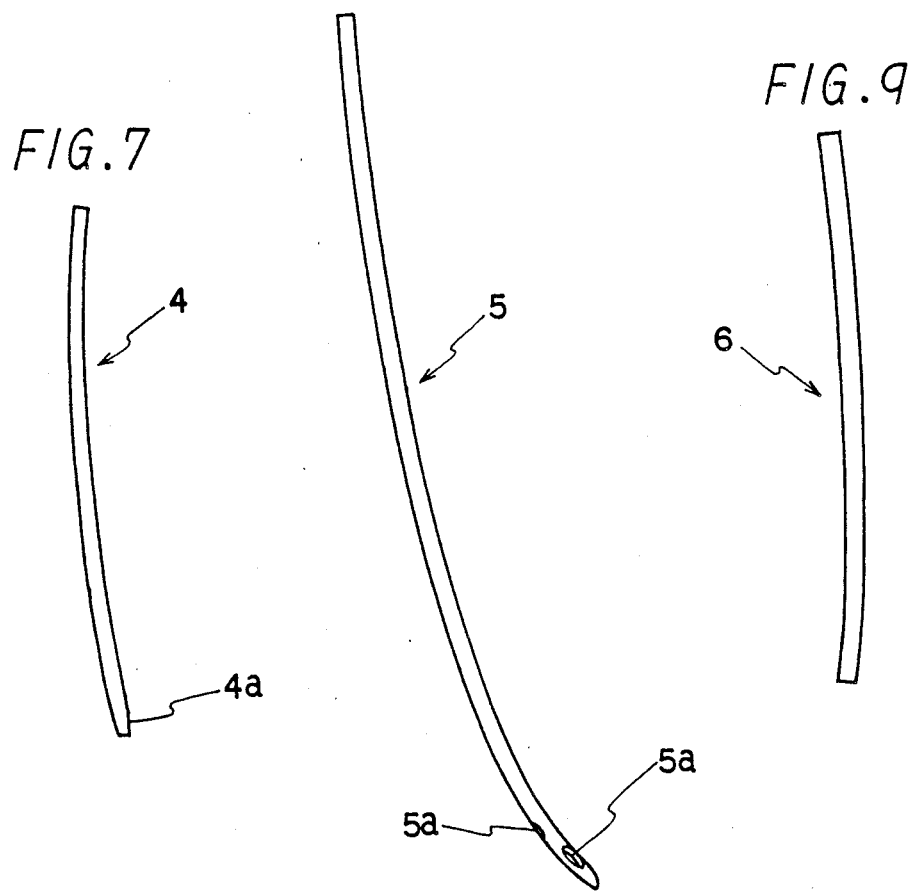
FIG.8
FIG.9
FIG.10
FIG.11

DEVICE FOR FORMING AN INSERTING HOLE FOR AN ENDOSCOPE

CROSS-REFERENCE TO RERATED APPLICATION

This is a continuation-in-part of application Ser.No. 198,005 filed on May 24, 1988 now abandoned.

BACKGROUND OF THE INVENTION

The present invention relates to a device for forming an inserting hole for an endoscope, and more particularly to a device used for forming an inserting hole for medical examination or treatment of various kinds of cholangia diseases, nephrosis and the like which enables the use of an endoscope just after the drainage and can surely prevent a drainage tube from dislodging off in the abdominal cavity.

In recent years, improvement has been made in the field of endoscopes so that percutaneous treatments using endoscopes have been carried out for various sickness in the bile duct, cholecyst, renal pelvis or ureter. That is, fibrous cells are formed around a drainage tube as a reaction of the organism to foreign material by percutaneously inserting the drainage tube having a diameter of 5 to 6 mm (1 mm is 3 frenches) necessary for the insertion of the endoscope into duct organs such as bile duct, cholecyst, renal pelvis and the like. A fistula is thus formed and the endoscope is put in or out through the fistula to carry out the treatment.

In the conventional technique, a small diameter tube (for example 7-french tube) is gradually exchanged at an interval of few days to one week for such tube as having one or 2 french larger outer diameter in about an month, whereby forming a large diameter fistula allowing the insertion of endoscopes. Thus, the conventional method has problems that it gives a great pain to a patient and is time-consuming.

With respect to the technique of dilation, USP 4,705,041 by Kim discloses a dilating tube for sphincter of Oddi. The Kim's tube comprises a guide catheter having an expandable tip and a plurality of dilators each having an enlarged tip portion at one end and a handle portion at the other end.

However, the Kim's tube is merely a device which dilates a narrowed portion and accordingly cannot be used for newly forming a fistula. Though the tip of the guide catheter in Kim's tube is made expandable to fascilitate the blind operation, such expandable tip is not necessary in the dilating operation using a device of the present invention because the operation of tubes is performed under fluoroscopy in the case of the device of the present invention.

Further, the ditator in Kim's tube has an enlarged portion at its end only for being pushed blindly to duodenum and dilating sphincter of Oddi after inserting a guide catheter through a cut bile duct during the ventrotomy.

The Kim's dilator, accordingly, cannot dilate a catheter tract in the liver tissue, in which veins and bile ducts extend like a mesh, in the way in which the dilator pushes its way through the tissue. Moreover, there are caused a hemorrhage from a tract and a leakage of bile, since the tip of the Kim's dilator is enlarged, and a difference in level between the enlarged tip and a portion succeeding the enlarged tip checks sufficient fitting between the dilator and the tract whereby generating a gap therebetween.

Still further, it is not easy to operate the Kim's dilator since it has a handle portion for operation and therefore is made long.

In order to solve the above-mentioned problem, the present inventor proposes a set for expanding a fistula for bile drainage (Japanese Unexamined Utility Model Publicatation No. 78938/1987). The set comprises a small diameter tube allowing a guide wire to pass through a center thereof, a medium diameter tube covering an outer periphery of the small diameter tube, and a large diameter tube covering the outer periphery of the small diameter tube and having an outer diameter larger than that of the medium diameter; and is characterized in that an outer diameter of each tip portion of the small diameter tube, the medium diameter tube and the large diameter tube is gradually reduced toward ends thereof to be taper-shaped.

Thanks to the use of the above set for expanding a fistula for bile drainage, a fistula is expanded only in about three to five minutes and the large diameter drainage tube can be inserted into the expanded fistula while, in the conventional technique, catheters are required to be exchanged four or five times at an interval of few days to one week.

In the various treatments using an endoscope such as lithotripsy, polypectomy and the recovery of the removed tissue, however, it is necessary to completely pull out the endoscope many times while holding the tissue or calculus. Therefore a fistula between the chest wall and he surface of the liver or between the retro abdominal wall and kidney is required to securely adhere. A large diameter drainage tube having a diameter of 16-french to 18-french is required to be kept in the fistula to complete the formation of a strong fistula. Such method gives a great pain to a patient.

It is an object of the present invention to provide a device for forming an inserting hole for an endoscope capable of reducing the damage of human body organization as much as possible and capable of not only expanding a fistula but also carrying out a treatment using an endoscope in a short time.

SUMMARY OF THE INVENTION

In accordance with the present invention, there is provided a device for forming an inserting hole for an endoscope comprising:

a metallic guide wire;

a small diameter tube made of slightly hard synthetic resin such as Teflon so as to be elastically bendable, and allowing the guide wire to pass through a center of the small diameter tube;

a medium diameter tube made of slightly hard synthetic resin covering an outer periphery of the small diameter tube;

a medium-large diameter tube made of slightly hard synthetic resin covering the outer periphery of the small diameter tube;

a large diameter tube covering the outer periphery of the small diameter tube, having an outer diameter larger than that of the medium-large diameter tube, and being made of slightly hard synthetic resin;

a large diameter drainage tube covering the outer periphery of the small diameter tube, having the same outer diameter as the large diameter tube, and being made of soft elastic material; and an extra large diameter tube having a thin wall and covering the outer periphery of the large diameter drainage tube, and being made of hard synthetic resin; wherein an outer diameter of each tip portion of the small diameter tube, the medium diameter tube, the medium-large diameter tube and the large diameter tube is gradually reduced toward ends thereof to be taper-shaped.

By inserting an extra large diameter tube having a thin wall and an inner diameter which is approximately the same as the outer diameter of a large diameter drainage tube into a bile duct or a cholecyst, the insertion and putting out of an endoscope can be easily carried out just after the drainage. Further, by inserting an extra large diameter tube into a fistula in the liver with covering a large diameter drainage tube, and by leaving the extra large diameter tube in the fistula and carrying out the drainage, a treatment using an endoscope can be completed within two or three days after the drainage.

BRIEF EXPLANATION OF THE DRAWINGS

FIG. 1 is an external view of a small diameter tube in the present invention;

FIG. 2 is an enlarged longitudinal sectional view of a tip portion of the small diameter tube of FIG. 1;

FIG. 3 is a lateral sectional view of the tip portion of FIG. 2;

FIG. 4 is an external view of a medium diameter tube in the present invention;

FIG. 5 is an enlarged longitudinal sectional view of a tip portion of the medium diameter tube of FIG. 4;

FIG. 6 is an external view of a medium-large diameter tube in the present invention;

FIG. 7 is an external view of a large diameter tube in the present invention;

FIG. 8 is an external view of a large diameter drainage tube in the present invention;

FIG. 9 is an external view of an extra large diameter tube in the present invention; and FIGS. 10 to 19 are sectional views of a liver showing a procedure of an operation of forming an inserting hole for an endoscope.

DETAILED DESCRIPTION

Figure 12:
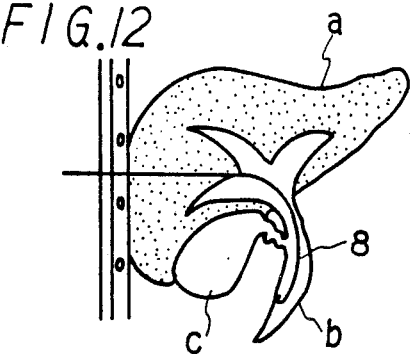

Next an embodiment of the present invention is explained based on the accompanying drawings.

FIG. 1 shows a small diameter tube 1 (called "dilater") having an outer diameter of 10-french, and fitting a metal-made guide wire having an inner diameter of 0.038 inch. The small diameter tube is made of Teflon and has a total length of about 50 cm. The small diameter tube has a high resiliency, and the outer diameter of a tip portion 1a thereof is gradually reduced toward its end to be taper-shaped as shown in FIG. 2 which shows an enlarged longitudinal sectional view of the tip portion 1a. FIG. 3 shows an enlarged lateral sectional view of the tip portion 1a.

FIG. 4 shows a medium diameter tube 2 having an inner diameter of 10-french so as to cover an outer periphery of the small diameter tube 1 and an outer diameter of 14-french. The medium diameter tube 2 is made of Teflon and has a total length of about 20 cm. The outer diameter of a tip portion 2a of the medium diameter tube 2 is gradually reduced like the small diameter tube 1 to be taper-shaped as shown in FIG. 5.

FIG. 6 shows a medium-large diameter tube 3 having an inner diameter of 10-french so as to cover the outer periphery of the small diameter tube 1 and an outer diameter of 16-french which is larger than that of the medium diameter tube 2. The medium-large diameter tube 3 is made of Teflon and has a total length of about 20 cm like the medium diameter tube 2. The outer diameter of a tip portion 3a of the medium-large diameter tube 3 is gradually reduced to be taper-shaped like the medium diameter tube 2.

Further, FIG. 7 shows a large diameter tube 4 having an inner diameter of 10-french so as to cover the outer periphery of the small diameter tube 1 and an outer diameter of 18-french which is larger than that of the medium-large diameter tube 3. The large diameter tube 4 is made of Teflon and has a total length of about 20 cm like the medium diameter tube 2. The outer diameter of a tip portion 4a of the large diameter tube 4 is gradually reduced to be taper-shaped like the medium diameter tube 2.

FIG. 8 shows a large diameter drainage tube 5 made of polyvinyl chloride, and having an inner diameter of 10-french so as to cover the outer periphery of the small diameter tube 1 and an outer diameter of 18-french which is equal to that of the large diameter tube 4. The large diameter drainage tube 5 has a total length of about 33 cm and has a high resiliency. Several side holes 5a are made on a tip portion of the drainage tube 5.

FIG. 9 shows an extra large diameter tube 6 made of Teflon, and having an inner diameter of 18-french so as to cover the outer periphery of the large diameter drainage tube 5 and an outer diameter of 19-french. The extra large diameter tube 6 has a total length of about 20 cm and is made of Teflon. The tube 6 is made thin provided that it has a suitable rigidity unlike the above-mentioned tubes 1 to 5.

An operation of forming a fistula for an endoscope using the above-mentioned small diameter tube 1, medium diameter tube 2, medium-large diameter tube 3, large diameter tube 4, large diameter drainage tube 5 and extra large diameter tube 6 is carried out in accordance with the following procedure or order.

Figure 13:
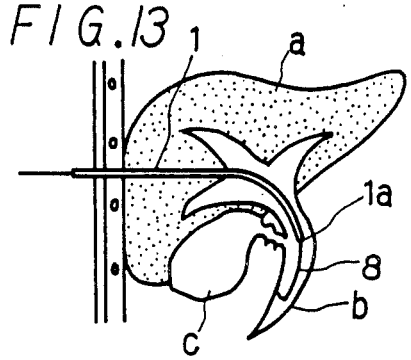
Figure 14:
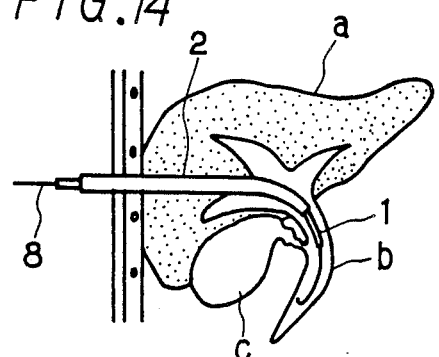
Figure 15:
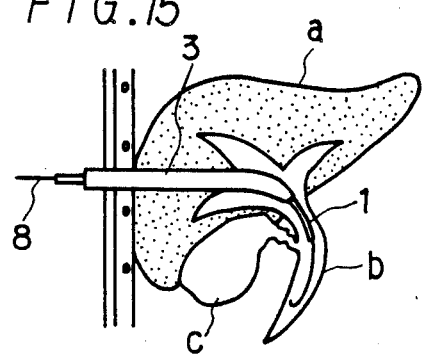
Figure 16:
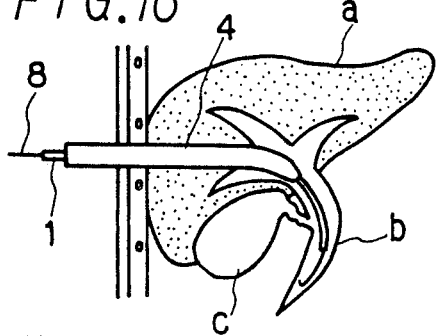
Figure 17:
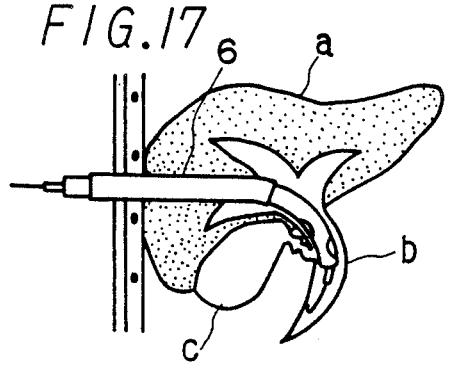
Figure 18:
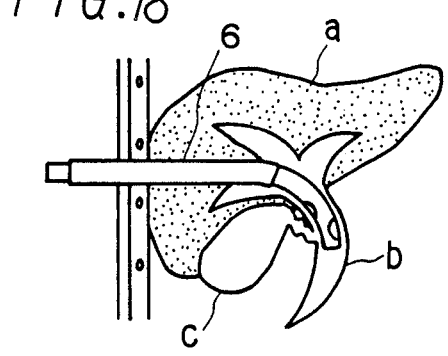
Figure 19:
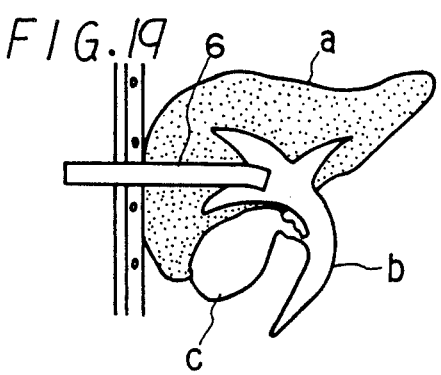

FIGS. 10 to 19 show an order of fistula-forming operation applied to an example of cholangia. In FIGS. 10 to 19, symbol a is a liver, symbol b is a bile duct, and symbol c is a cholecyst. FIG. 10 shows a state wherein a small diameter drainage tube 7 is inserted into the cholangia in a percutaneous manner. First of all, a metallic guide wire 8 is inserted into the tube 7 (see FIG. 11). The guide wire 8 is called "J guide wire" of which tip portion has a characteristic of elastically bending in a J-shaped manner. The guide wire 8 is inserted into the tube 7 with keeping the tip portion thereof straight, and the tip portion curves in a J-shaped manner when it projects from an opening of the tip portion of the tube, so that the bile duct is not damaged. Next, the small diameter drainage tube 7 is pulled out while leaving the guide wire 8 as it is as shown in FIG. 12. Then the small diameter tube 1 having an outer diameter of 10-french is put on the guide wire 8 and is inserted into the bile duct as shown in FIG. 13. At this stage, the fistula is expanded to 10-french. The medium diameter tube 2 is put on the small diameter tube 1 and is inserted with being rotated to the vicinity of the porta hepatis, whereby the diameter of the fistula is enlarged to 14-french. Next, only the medium diameter tube 2 is pulled out while leaving the small diameter tube 1. The medium-large diameter tube 3 is put on the small diameter tube 1 instead of the medium diameter tube 2 as shown in FIG. 15, and is inserted into the bile duct with being rotated whereby the diameter of the fistula is enlarged to 16- french. After pulling out the medium-large diameter tube 3, the large diameter tube 4 is put on the small diameter tube 1 as shown in FIG. 16, and is inserted into the bile duct with being rotated whereby the diameter of the fistula is enlarged to 18-french. Then the large diameter tube 4 is pulled out, and the large diameter drainage tube 5 is put on the small diameter tube 1 and is sufficiently inserted into the bile duct with leaving the extra large diameter tube 6 on the small diameter tube 1. The large diameter drainage tube 5 has an outer diameter equal to that of the large diameter tube 4, so that it can be inserted into the bile duct without resistance even when it is made of soft resilient material. The extra large diameter tube 6 is inserted into the bile duct with being rotated till a tip portion of the tube 6 reaches a position a few centimeters before a tip portion of the large diameter drainage tube 5, so as to further expand the fistula. After the extra large tube 6 reaches the inner cavity of the bile duct, the small diameter tube 1 and the guide wire 8 are pulled out as shown in FIG. 18, whereby the bile drainage becomes possible. On inserting an endoscope, the large diameter drainage tube 5 is pulled out while keeping the extra large diameter tube 6 as it is as shown in FIG. 19. By the pulling out of the drainage tube 5, any endoscope having an outer diameter less than that of the extra large diameter tube 6 can be inserted into the bile duct. Polypectomy, recovery of the removed tissue and extraction of the calculus in addition to biopsy can be smoothly carried out. After the medical treatment is over, the large diameter drainage tube is inserted into the bile duct through the extra large diameter tube 6 to perform the percutaneous drainage. The present inventor applies the fistula-forming operation to several cases of various cholangia diseases such as choledocholithiasis, choledochiarctia, cholecystolithiasis and cholecystic polyp, ureterostenosis and ureterolithiasis. In all cases, the extra large diameter tube can be inserted in percutaneous manner not only into the bile duct shown in the drawing but also into the cholecyst or renal pelvis. During the operation no complication was recognized.

Though the small diameter tube 1, medium diameter tube 2, medium-large diameter tube 3, large diameter tube 4 and extra large diameter tube 6 in the above embodiment are made of Teflon, other synthetic resin material, for example reinforced polyethylene, can also be used. Synthetic resin having soft resiliency can be used besides polyvinyl chloride as a material for the large diameter drainage tube 5.

It should be noted that the inner diameter and outer diameter of each tube are not limited to those stated in the embodiment. FIGS. 10 to 19 show an operation of forming a fistula for an endoscope with respect to the bile duct. Fistula can be formed by the same method in the gallbladder or renal pelvis.

According to a device for forming an inserting hole for an endoscope which includes a small diameter tube, a medium diameter tube, a medium-large diameter tube and a large diameter tube, an outer diameter of each tip portion of the tubes is gradually reduced toward its end to be taper-shaped. Accordingly, when the small diameter tube is inserted into the human body with covering a guide wire and when the medium diameter tube, medium-large diameter tube and large diameter tube are inserted with covering the small diameter tube, breakdown of the tissue is hardly taken place and hemostatic effect can be obtained since the tapered surface of the tube in contact with the inner surface of the fistula presses liver organization or subcutaneous tissue and gradually expand the fistula.

Further, in the case of the conventional endoscope treatment such as polypectomy requiring the insertion and pulling out of the endoscope, the period of forming a fistula of about three weeks was required until the fistula between the chest wall and the surface of the liver was sufficiently formed. However, by the use of an extra large diameter tube in the present invention which can function as a fistula, the period of forming the fistula is not at all required and the endoscope can be inserted into and pulled out from the human body instantly and safely. The period required for the treatment can be shortened and pains of the patient can be minimized.

Further, in the conventional method, a drainage tube is sutured to the skin of a patient every time a treatment using an endoscope is carried out, so that the patient suffered from a great pain. However, in the device of the present invention, an extra large diameter tube is sutured when the first drainage operation is carried out. Therefore, it is sufficient to connect a newly inserted drainage tube to the extra large diameter tube with a thread when the succeeding endoscope treatment is finished. That is, it is not necessary to suture a drainage tube to the skin every time it is used.

The dislodgement of the drainage tube in the abdominal cavity, which sometimes occurs due to the bending of the tube on the liver surface caused by movement of a patient, can be surely avoided since the extra large diameter tube is left in the human body together with the drainage tube. The dislodgement of the drainage tube in the abdominal cavity causes a very serious complication such as bile peritonitis. Such situation is a matter of life of the patient and requires an urgent drainage.

What is claimed is:

1. A kit for forming an increasingly large opening through the skin for the sequential draining of liquid and the insertion of an endoscope, said kit comprising
   (a) a metallic guide wire,
   (b) a small diameter synthetic resin tube (1) that is elastically bendable and has a central passage which can accommodate within it said metallic guide wire,
   (c) a medium diameter synthetic resin tube having an inner diameter slightly larger than the outer periphery of said small diameter tube so that it will fit closely around the exterior periphery of the small diameter tube (1);
   (d) a medium-large diameter flexible synthetic resin tube (3) having an inner diameter only slightly larger than the outer diameter of said small diameter tube (1) so that it will fit closely around the exterior periphery of the small diameter tube (1) when said medium diameter tube (2) is no longer surrounding said small diameter tube (1), but an outer diameter larger than said medium diameter tube (2);
   (e) a large diameter synthetic resin tube (4) having an inner diameter only slightly larger than the outer diameter of said small diameter tube (1) so that it will fit closely around the exterior periphery of the small diameter tube (1) when said medium-large diameter tube (3) is no longer when said medium-large diameter tube (3) is no longer surrounding said small diameter tube (1), but an outer diameter larger tan said medium-large diameter tube (3);

(f) a drainage tube (5) of soft elastic synthetic resin having an inner diameter only slightly larger than the outer diameter of said small diameter tube (1) so that it will fit closely around the exterior periphery of the small diameter tube (1) when said large diameter tube (4) is no longer surrounding said small diameter tube (1) and an outer diameter the same as said large diameter tube (4), and (g) an extra large diameter tube (6) made of hard synthetic resin having an inner diameter only slightly larger than the outer diameter of said drainage tube (5), so that it will fit closely around the exterior periphery of said drainage tube (5), and wherein each of said tubes having outer and inner ends, the inner ends of said small, medium, medium-large and large diameter tubes (1, 2, 3 & 4) being of reduced diameter so as to thereby form tapered inner ends, the inner end of said drainage tube (5) being provided with several openings (5a).

2. A kit according to claim 1 wherein said small diameter tube (1) has an outer diameter of 10-french
and a length of 50 cm, said medium diameter tube (2) has an inner diameter of about 10 french, an outer diameter of 14-french and a length of about 20 cm, said medium-large tube (3) has an inner diameter of about 20-french, an outer diameter of 16-french and a length of about 20 cm, said large diameter tube (4) has an inner diameter of about 10-french, an outer diameter of about 18-french and a length of about 20 cm, said drainage tube (5) has an inner diameter of about 10-french, an outer diameter of 18-french, and a length of about 33 cm, and said large tube (6) has an inner diameter of 18-french an outer diameter of 19-french and a length of about 20 cm.

3. A kit according to claim 1 wherein said small, medium, medium-large, large and extra-large tubes (1, 2, 3, 4 and 6) are made of Teflon.

4. A kit according to claim 1 wherein said small, medium, medium-large, large and extra-large tubes (1, 2, 3, 4 and 6) are made of reinforced polyethylene.

5. A kit according to claim 2 wherein said small, medium, medium-large, large and extra-large tubes (1, 2, 3, 4 and 6) are made of Teflon.

6. A kit according to claim 2 wherein said small, medium, medium-large, large and extra-large tubes (1, 2, 3, 4 and 6) are made of reinforced polyethylene.

7. A kit according to claim 3 wherein said drainage tube (5) is made of polyvinyl chloride.

8. A kit according to claim 4 wherein said drainage tube (5) is made of polyvinyl chloride.

* * * * *